United States Patent
Fadini et al.

(10) Patent No.: US 10,005,803 B2
(45) Date of Patent: Jun. 26, 2018

(54) CRYSTALLINE FORMS OF FOSNETUPITANT

(71) Applicant: Helsinn Healthcare SA, Lugano/Pazzallo (CH)

(72) Inventors: Luca Fadini, Biasca (CH); Alessio Venturini, Varese (IT)

(73) Assignee: Helsinn Healthcare SA, Lugano/Pazzallo (CH)

( * ) Notice: Subject to any disclaimer, the term of this patent is extended or adjusted under 35 U.S.C. 154(b) by 0 days. days.

(21) Appl. No.: 15/282,016

(22) Filed: Sep. 30, 2016

(65) Prior Publication Data

US 2017/0096442 A1 Apr. 6, 2017

Related U.S. Application Data

(60) Provisional application No. 62/237,839, filed on Oct. 6, 2015.

(51) Int. Cl.
*C07F 9/6509* (2006.01)
*C07F 9/09* (2006.01)

(52) U.S. Cl.
CPC ........ *C07F 9/650958* (2013.01); *C07F 9/091* (2013.01); *C07B 2200/13* (2013.01)

(58) Field of Classification Search
None
See application file for complete search history.

(56) References Cited

U.S. PATENT DOCUMENTS 5,972,938 A 10/1999 Rupniak et al.

FOREIGN PATENT DOCUMENTS

| WO | 95/16679 A1 | 6/1995 |
| WO | 95/18124 A1 | 7/1995 |
| WO | 95/23798 A1 | 9/1995 |
| WO | 2013/082102 A1 | 6/2013 |

OTHER PUBLICATIONS

Neurosci. Res., 1996, 7,187-214, Barker.
Can. J. Phys., 1997, 75, 612-621, Longmore et al.
Science, 1998,281, 1640-1645, Kramer et al.
Maggi, et al. "Tachykinin Receptor and Tachykinin Receptor Antagonists", J. Auton. Pharmacol., 13,23-93, 1993.
Navari, et al. The New England Journal of Medicine, vol. 340, No. 3 190-195, 1999.

*Primary Examiner* — Emily Bernhardt
(74) *Attorney, Agent, or Firm* — Clark G Sullivan

(57) ABSTRACT

The present invention provides crystalline forms of the chloride monohydrochloride salt of fosnetupitant, methods of making the crystalline forms, and pharmaceutical dosage forms that make use of the crystalline forms.

23 Claims, 8 Drawing Sheets
(8 of 8 Drawing Sheet(s) Filed in Color)

CRYSTALLINE FORMS OF FOSNETUPITANT

FIELD OF THE INVENTION

The present invention is related to crystalline forms of fosnetupitant, particularly the chloride monohydrochloride salt of fosnetupitant. The invention also relates to methods of making crystalline forms of fosnetupitant, and pharmaceutical dosage forms that make use of these crystalline forms.

BACKGROUND OF THE INVENTION

Polymorphism refers to the ability of a compound to assume at least two crystalline arrangements in the solid state. In the pharmaceutical industry, the polymorphic form of an active pharmaceutical ingredient (API) is relevant because it can affect the solubility and bioavailability of the drug. Consideration of polymorphism also helps reduce the risk of problems and costs during large scale production.

Fosnetupitant is a neurokynin-1 ("NK-1") antagonist under development by Helsinn Healthcare SA, Lugano/Pazzallo Switzerland, for the treatment of chemotherapy induced nausea and vomiting. The compound is known chemically as 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium, and has the following chemical structure in its acidic/free base form:

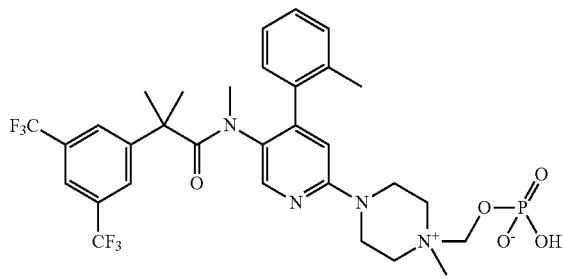 [SMILES: Cc1ccccc1-c1cc(N2CC[N+](C)(COP(=O)([O-])O)CC2)ncc1N(C)C(=O)C(C)(C)c1cc(C(F)(F)F)cc(C(F)(F)F)c1]

The chloride monohydrochloride salt, and a method for its preparation, is described in WO 2013/082102. The chemical structure for this salt is reported as follows:

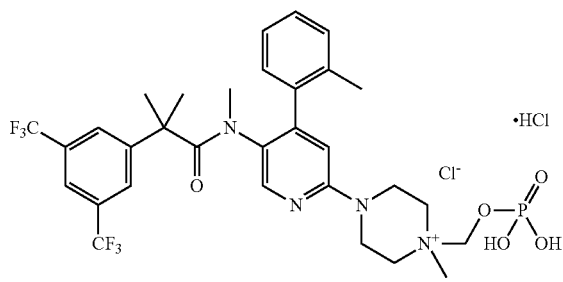 [SMILES: Cc1ccccc1-c1cc(N2CC[N+](C)(COP(=O)(O)O)CC2)ncc1N(C)C(=O)C(C)(C)c1cc(C(F)(F)F)cc(C(F)(F)F)c1 ; [Cl-] ; Cl]

The molecule can be challenging to manufacture, particularly in a highly pure crystalline form in a commercially acceptable yield. Solvents used in the manufacture of the product pose special challenges. Prior art processes have removed these solvents via evaporative techniques, which can degrade the fosnetupitant due to the excessive heat.

Accordingly, it is an object of the present invention to provide novel crystalline forms of fosnetupitant, with improved purity, stability and ease of manufacture.

Another object of the present invention is to provide methods for making these crystalline forms.

Yet another object is to provide pharmaceutical dosage forms that make use of these novel crystalline forms, including methods of making such pharmaceutical dosage forms.

Still another object is to provide improved methods for isolating and purifying fosnetupitant without degrading the product.

SUMMARY OF THE INVENTION

The present invention relates to crystalline forms of the chloride monohydrochloride salt of fosnetupitant, methods of making crystalline forms of fosnetupitant, and pharmaceutical dosage forms that make use of these crystalline forms.

In one aspect the invention provides a crystalline form of the chloride hydrochloride salt of (4-(5-(2-(3,5-bis(trifluoromethyl)phenyl)-N,2-dimethylpropanamido)-4-(o-tolyl)pyridin-2-yl)-1-methylpiperazin-1-ium-1-yl)methyl hydrogen phosphate (fosnetupitant) which is Form I ("Form I fosnetupitant"), comprising less than 1.0 or 0.5 wt. % of the dimer of fosnetupitant, and less than 1.0 or 0.5 wt. % of 2-(3,5-bis(trifluoromethyl)phenyl)-N,2-dimethyl-N-(6-(4-methylpiperazin-1-yl)-4-(o-tolyl)pyridin-3-yl)propanamide (netupitant). The Form I can be characterized by the XRPD patterns described in greater detail herein, or any of the other methods of characterization described herein. Still further embodiments relate to Forms II and III fosnetupitant, and to methods of making these crystalline forms, as described in greater detail herein.

The foregoing and other objects, features and advantages of the invention will be apparent from the following more particular description of preferred embodiments of the invention.

BRIEF DESCRIPTION OF THE DRAWINGS

This patent application file contains at least one drawing executed in color. Copies of this patent application with color drawing(s) will be provided by the Office upon request and payment of the necessary fee.

DETAILED DESCRIPTION OF THE INVENTION

Figure 1:
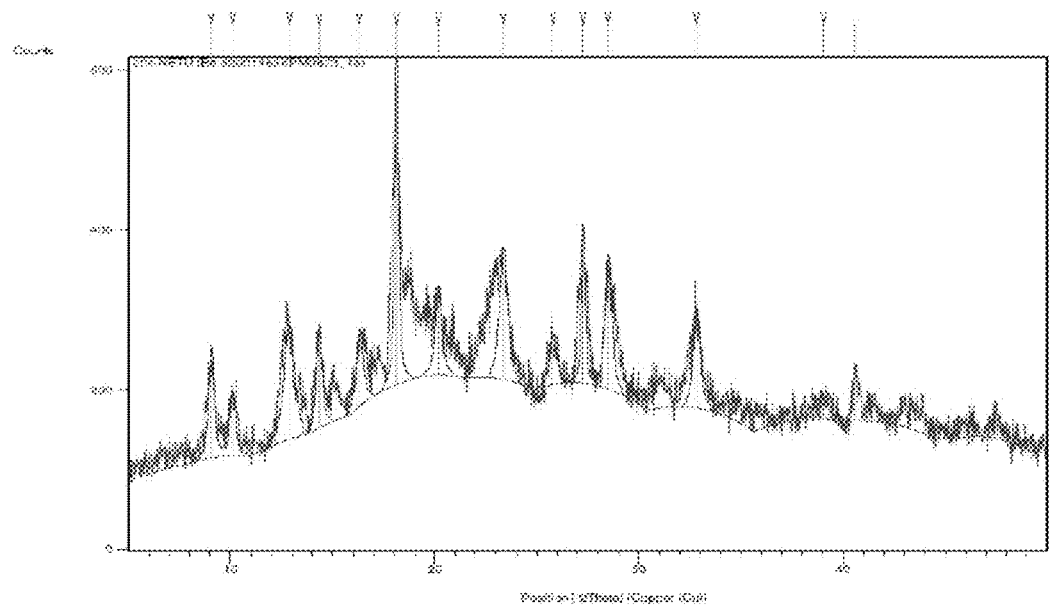
FIG. 1 is an X-Ray Powder Diffraction (XRPD) pattern of Form I generated according to the procedures described in Example 1.

The present invention may be understood more readily by reference to the following detailed description of preferred embodiments of the invention and the Examples included therein.

Definitions

As used in the specification and claims, the singular forms a, an, and the include plural references unless the context clearly dictates otherwise. For example, the term "a pharmaceutical excipient" refers to one or more pharmaceutical excipients for use in the presently disclosed formulations and methods.

When ranges are given by specifying the lower end of a range separately from the upper end of the range, it will be understood that the range can be defined by selectively combining any one of the lower end variables with any one of the upper end variables that is mathematically possible.

When used herein the term "about" will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength.

DISCUSSION

The present invention relates to crystalline forms of the chloride hydrochloride salt of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium, also known as fosnetupitant, represented by the following chemical structure:

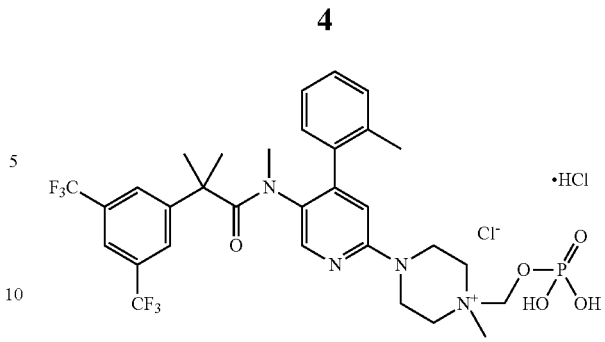

The term "fosnetupitant" is used herein to refer to 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium as well as the chloride hydrochloride salt of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium, depending on the particular context.

Typically, different crystalline forms of the same substance have different bulk properties related to, for example, hygroscopicity, solubility, stability, and the like. Forms with high melting points often have good thermodynamic stability which is advantageous in prolonging shelf-life of drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-Ray Powder Diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of fosnetupitant include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2θ values. Thus, peak assignments, such as those reported herein, can vary by plus or minus about 0.2° (2θ), and the term "substantially" as used in the context of XRPD herein is meant to encompass the above-mentioned variations. Alternatively, the 2θ values of an XRPD pattern can be characterized by a variance of plus or minus about 0.1°.

In the same way, temperature readings in connection with DSC, TGA, or other thermal experiments can vary about ±4° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±4° C. Accordingly, a crystalline form reported herein having a DSC thermogram "substantially" as shown in any of the Figures is understood to accommodate such variation.

Fosnetupitant can be isolated in numerous crystalline forms, including crystalline forms which are anhydrous, hydrated, non-solvated, or solvated. Example hydrates include hemihydrates, monohydrates, dihydrates, and the like. In some embodiments, the crystalline form of fosnetupitant is anhydrous and non-solvated. By "anhydrous" is meant that the crystalline form of fosnetupitant contains essentially no bound water in the crystal lattice structure, i.e., the compound does not form a crystalline hydrate.

Fosnetupitant can also be isolated as a clathrate such that the stoichiometry of water to fosnetupitant in the crystalline lattice can vary without impacting the crystalline structure of the molecule. The degree of hydration (i.e. stoichiometric ratio of water to compound of Formula I) can range from greater than zero to as much as 3 without changing the crystalline form of the molecule. In some embodiments, fosnetupitant has a degree of hydration of from 0.5 to 2.5. In other embodiments, the crystalline form of fosnetupitant has a degree of hydration of from 1.0 to 2.0. Moreover, in any of these embodiments, the crystalline clathrate can further include an organic volatile impurity without impacting the crystalline structure of the molecule, such as methanol, ethanol, methyl acetate or isopropanol.

In some embodiments, the crystalline forms of the invention are substantially isolated. By "substantially isolated" is meant that a particular crystalline form of fosnetupitant is at least partially isolated from impurities. For example, in some embodiments, a crystalline form of the invention comprises less than about 50%, less than about 40%, less than about 30%, less than about 20%, less than about 15%, less than about 10%, less than about 5%, less than about 3%, less than about 1%, or less than about 0.5% of impurities. An impurity is defined herein to include degradants, reaction by-products, and other related compounds, but to exclude water and organic volatile impurities.

In one particular embodiment, the invention provides crystalline forms of fosnetupitant, including pharmaceutical dosage forms that make use of such crystalline forms, that contain less than 1%, 0.5%, or 0.3% of the dimer of fosnetupitant or the parent molecule.

The dimer of fosnetupitant refers to 4-(5-{2-[3,5-bis(trifluoromethyl)phenyl]-N,2-dimethylpropanamido}-4-(2-methylphenyl)pyridin-2-yl)-1-[({[4-(5-{2-[3,5-bis(trifluoromethyl) phenyl]-N,2-dimethylpropanamido}-4-(2-methylphenyl)pyridin-2-yl)-1-methylpiperazin-1-ium-1-yl] methyl phosphonato}oxy)methyl]-1-methylpiperazin-1-ium chloride, having the following chemical structure:

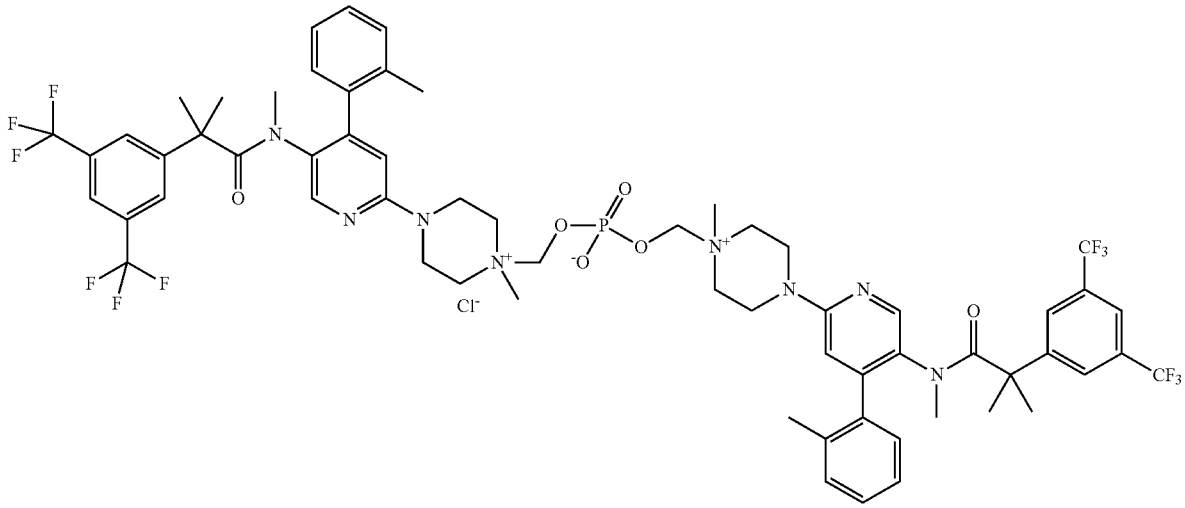

The parent molecule refers to netupitant or a salt thereof, chemically known as 2-(3,5-bis(trifluoromethyl)phenyl)-N, 2-dimethyl-N-(6-(4-methylpiperazin-1-yl)-4-(o-tolyl)pyridin-3-yl)propanamide.

In some embodiments, a crystalline form of fosnetupitant is substantially free of other crystalline forms. The phrase "substantially free of other crystalline forms" means that a particular crystalline form of fosnetupitant comprises greater than about 80%, greater than about 90%, greater than about 95%, greater than about 98%, greater than about 99%, or greater than about 99.5% by weight of the particular crystalline form. However, as discussed in the examples hereto, each of the crystalline forms of the present invention typically exists in the presence of some quantity of the amorphous form.

Form I XRPD Characterization

Figure 14:
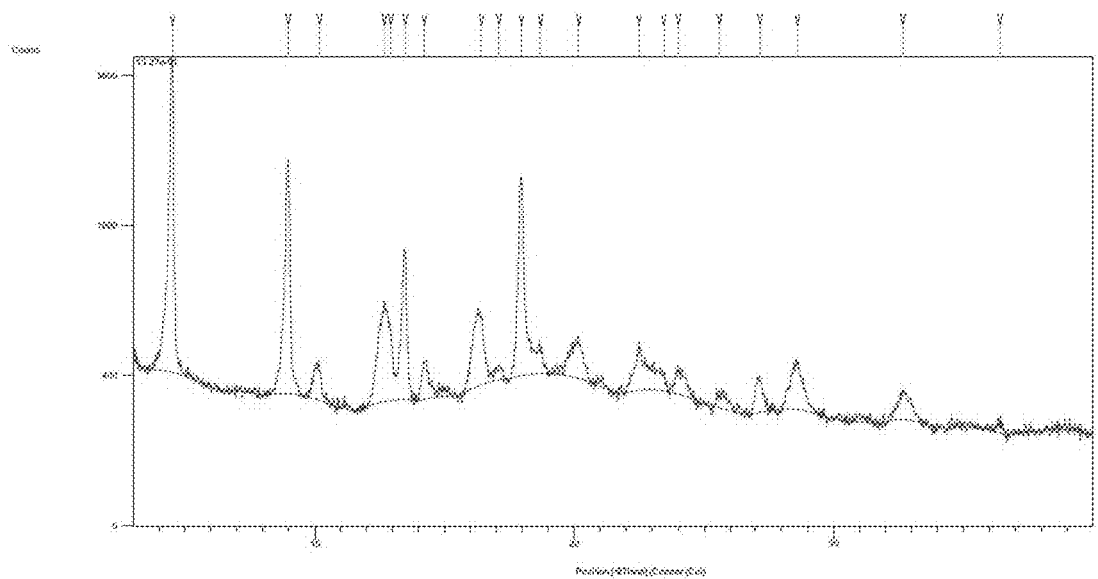
FIG. 14 is an X-Ray Powder Diffraction (XRPD) spectrum of Form I generated according to the procedures of Example 2.
Figure 15:
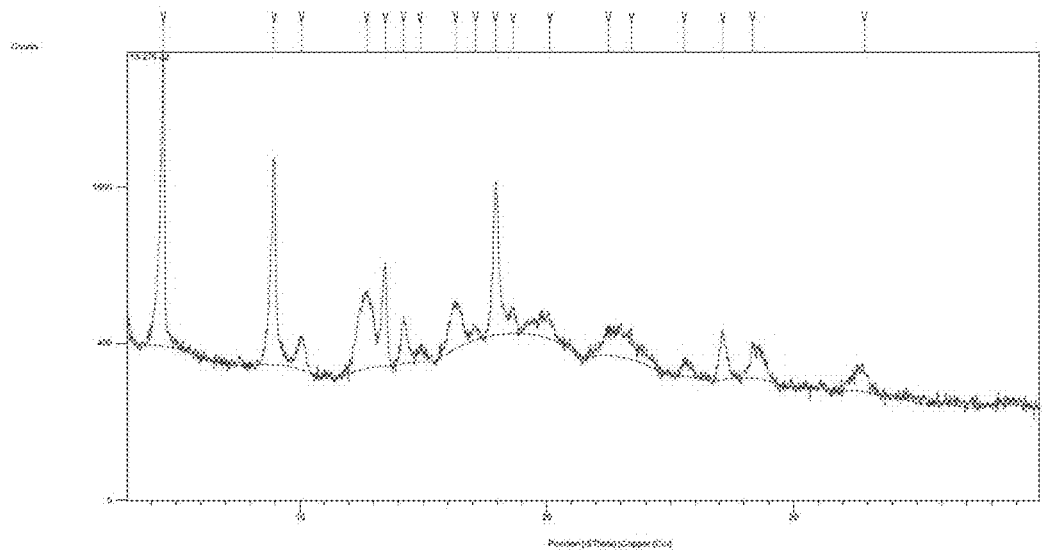
FIG. 15 is an X-Ray Powder Diffraction (XRPD) spectrum of Form I generated according to the procedures of Example 2.

Form I is preferably characterized by XRPD spectra, and in one embodiment Form I is substantially characterized by the XRPD pattern depicted in FIG. 1, 14 or 15.

In another embodiment Form I is characterized as exhibiting three, four, five, six seven, eight or more of any combination of the characteristic peaks set forth in Table 2.a or 2.b.

In another embodiment Form I is characterized as exhibiting three, four, five, six seven, eight or more of any combination of the following characteristic peaks: 4.5, 9.0, 10.1, 12.7, 13.5, 14.2, 16.3, 17.9, 18.6, 22.5, 23.4, 27.1, and 28.4.

In another embodiment Form I is characterized as exhibiting at least three of the following characteristic peaks: 4.5, 9.0, 12.7, 13.5, 16.3, and 17.9.

In another embodiment Form I is characterized as exhibiting at least four of the following characteristic peaks: 4.5, 9.0, 12.7, 13.5, 16.3, and 17.9.

In another embodiment Form I is characterized as exhibiting at least five of the following characteristic peaks: 4.5, 9.0, 12.7, 13.5, 16.3, and 17.9.

In another embodiment Form I is characterized as exhibiting the following characteristic peaks: 4.5, 9.0, 12.7, 13.5, 16.3, and 17.9.

Each of the foregoing characteristic peaks, including those depicted in FIGS. 1, 14 and 15, is preferably modified by a level of variability equaling +/−0.2 degrees or +/−0.1 degrees.

In a particularly preferred embodiment, the Form I fosnetupitant comprises less than 1.0, 0.5, or 0.3 wt. % of the dimer of fosnetupitant, and less than 0.5 wt. % of 2-(3,5-bis(trifluoromethyl)phenyl)-N,2-dimethyl-N-(6-(4-methyl-piperazin-1-yl)-4-(o-tolyl)pyridin-3-yl)propanamide.

In still another embodiment, the Form I fosnetupitant is partially hydrated, in an amount of from about 0.3 to about 0.7 wt. %, or about 0.5 wt %.

Form II XRPD Characterization

Figure 6:
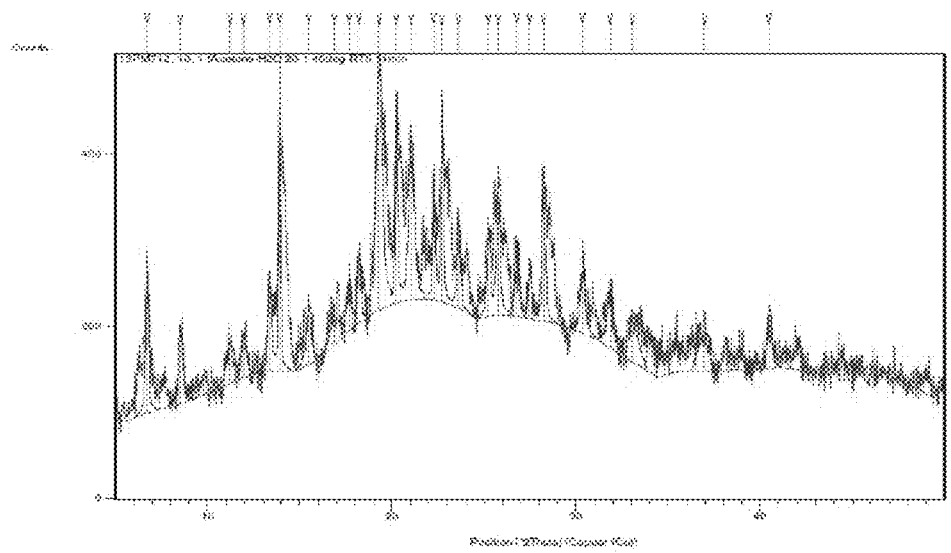
FIG. 6 is an X-Ray Powder Diffraction (XRPD) pattern of Form II generated according to the procedures described in Example 1.
Figure 16:
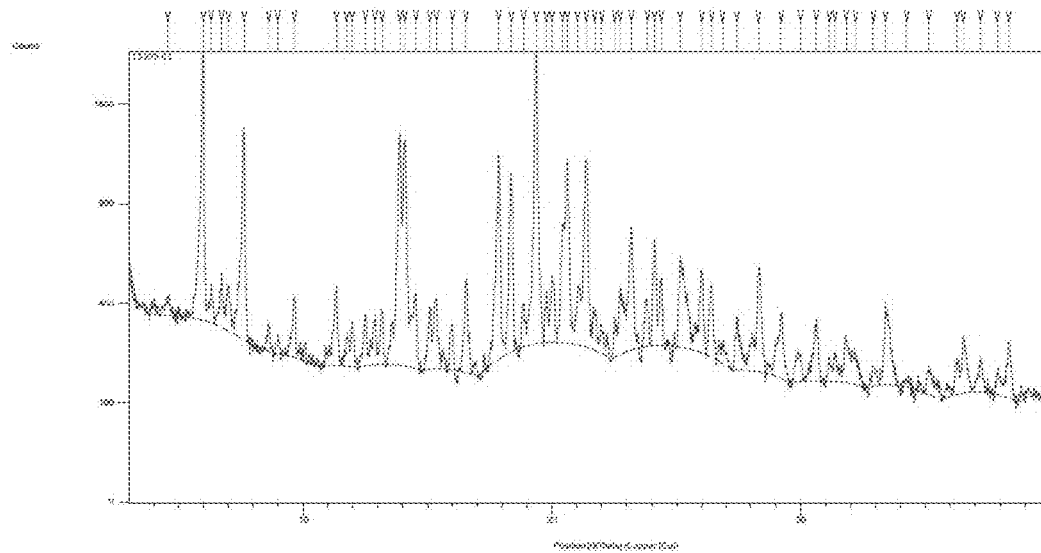
FIG. 16 is an X-Ray Powder Diffraction (XRPD) spectrum of Form II generated according to the procedures of Example 2.

Form II is preferably characterized by XRPD spectra, and in one embodiment Form I is substantially characterized by the XRPD pattern depicted in FIG. 6 or 16.

In another embodiment Form I is characterized as exhibiting three, four, five, six seven, eight or more of any combination of the characteristic peaks set forth in Table 2.c.

In another embodiment Form II is characterized as exhibiting three, four, five, six seven, eight or more of any combination of the following characteristic peaks: 6.0, 6.7, 7.0, 7.6, 8.6, 9.7, 11.3, 11.8, 12.0, 12.5, 12.9, 13.2, 14.1, 15.3, 16.0, 16.5, 17.9, 18.4, 18.9, 19.4, 20.0, 20.6, 21.4, 21.7, 22.7, 23.2, 23.8, 24.4, 25.1, 26.0, 27.4, 28.3, 29.2, 30.6, 31.8, 33.4, 36.3, 37.2, 38.3.

In another embodiment Form II is characterized as exhibiting three, four, five, six seven, eight or more of any combination of the following characteristic peaks: 6.0, 6.7, 7.6, 9.7, 11.3, 14.1, 15.3, 17.9, 18.4, 19.4, 20.0, 20.6, 21.4, 22.7, 23.2, 25.1, 26.0, 28.3, 29.2, 33.4.

In another embodiment Form II is characterized as exhibiting at least three of the following characteristic peaks: 6.0, 6.7, 7.6, 9.7, 11.3, 14.1, 15.3, 17.9, 18.4, 19.4, 20.0, 20.6, 21.4, 22.7, 23.2, 25.1, 26.0, 28.3, 29.2, 33.4.

In another embodiment Form II is characterized as exhibiting at least four of the following characteristic peaks: 6.0, 6.7, 7.6, 9.7, 11.3, 14.1, 15.3, 17.9, 18.4, 19.4, 20.0, 20.6, 21.4, 22.7, 23.2, 25.1, 26.0, 28.3, 29.2, 33.4.

In another embodiment Form II is characterized as exhibiting at least five of the following characteristic peaks: 6.0, 6.7, 7.6, 9.7, 11.3, 14.1, 15.3, 17.9, 18.4, 19.4, 20.0, 20.6, 21.4, 22.7, 23.2, 25.1, 26.0, 28.3, 29.2, 33.4.

In another embodiment Form II is characterized as exhibiting the following characteristic peaks: 6.0, 6.7, 7.6, 9.7, 11.3, 14.1, 15.3, 17.9, 18.4, 19.4, 20.0, 20.6, 21.4, 22.7, 23.2, 25.1, 26.0, 28.3, 29.2, 33.4.

In another embodiment Form II is characterized as exhibiting at least three of the following characteristic peaks: 6.0, 7.6, 14.1, 17.9, 19.4, 20.6, and 21.4.

In another embodiment Form II is characterized as exhibiting at least four of the following characteristic peaks: 6.0, 7.6, 14.1, 17.9, 19.4, 20.6, and 21.4.

In another embodiment Form II is characterized as exhibiting at least five of the following characteristic peaks: 6.0, 7.6, 14.1, 17.9, 19.4, 20.6, and 21.4.

In another embodiment Form II is characterized as exhibiting the following characteristic peaks: 6.0, 7.6, 14.1, 17.9, 19.4, 20.6, and 21.4.

Each of the foregoing characteristic peaks, including those displayed in FIGS. 6 and 16, is preferably modified by a level of variability equaling +/−0.2 degrees or +/−0.1 degrees.

In a particularly preferred embodiment, the Form II fosnetupitant comprises less than 1.0, 0.5, or 0.3 wt. % of the dimer of fosnetupitant, and less than 0.5 wt. % of 2-(3,5-bis(trifluoromethyl)phenyl)-N,2-dimethyl-N-(6-(4-methyl-piperazin-1-yl)-4-(o-tolyl)pyridin-3-yl)propanamide.

In still another embodiment, the Form II fosnetupitant is partially hydrated and exists as the monohydrate.

Form III XRPD Characterization

Figure 11:
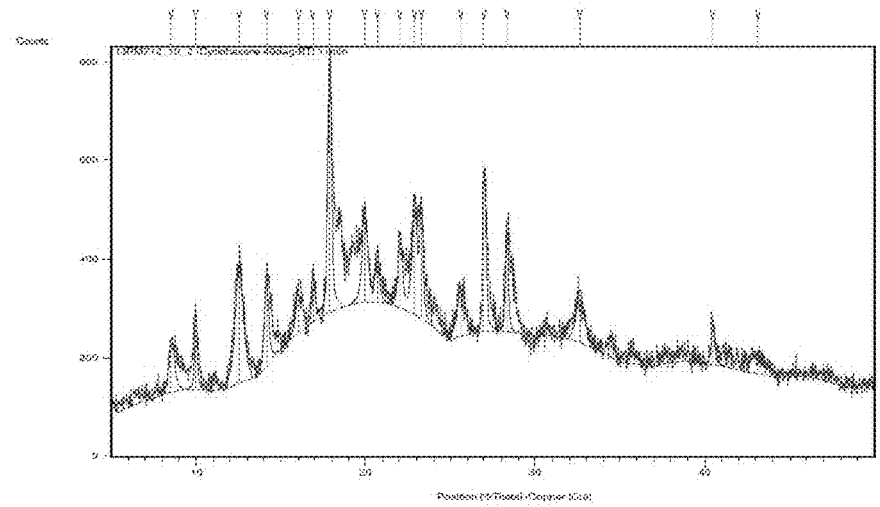
FIG. 11 is an X-Ray Powder Diffraction (XRPD) pattern of Form III generated according to the procedures described in Example 1.

Form III is preferably characterized by XRPD spectra, and in one embodiment Form III is substantially characterized by the XRPD pattern depicted in FIG. 11.

Each of the characteristic peaks in FIG. 11 is preferably modified by a level of variability equaling +/−0.2 degrees or +/−0.1 degrees.

In a particularly preferred embodiment, the Form III fosnetupitant comprises less than 1.0, 0.5, or 0.3 wt. % of the dimer of fosnetupitant, and less than 0.5 wt. % of 2-(3,5-bis(trifluoromethyl)phenyl)-N,2-dimethyl-N-(6-(4-methyl-piperazin-1-yl)-4-(o-tolyl)pyri din-3-yl)propanamide.

Methods of Making the Crystalline Forms of Fosnetupitant

Methods of making the crystalline forms of fosnetupitant of the present invention are described in the examples hereto. In one particular embodiment, the invention provides a method of making the Form I fosnetupitant of claim 1 comprising (a) contacting the chloride hydrochloride salt of fosnetupitant with methylacetate and methanol to form a first liquid; (b) separating the methylacetate and methanol from the chloride hydrochloride salt of fosnetupitant of step (a); (c) contacting the chloride hydrochloride salt of fosnetupitant from step (b) with heptane to form a second liquid; and (d) separating the heptane from the chloride hydrochloride salt of fosnetupitant of step (c).

In various subembodiments, step (a) further comprises contacting said chloride hydrochloride salt of fosnetupitant with hydrochloric acid, step (b) comprises evaporating said methanol from said first liquid product of step (a), and step (d) comprises evaporating said heptane from said second liquid at a pressure less than atmospheric and a temperature of from 20 to 50° C.

Still other embodiments relate to methods for producing Forms II and III. Thus, in one embodiment the invention provides a process for preparing Form II fosnetupitant comprising: (a) combining the chloride hydrochloride salt of fosnetupitant with a solution comprising acetone and water to provide a mixture; (b) slurrying the mixture; (c) filtering the slurried mixture; and (d) isolating a crystalline solid of Form II fosnetupitant.

In another embodiment the invention provides a process for preparing Form III fosnetupitant comprising (a) combining the chloride hydrochloride salt of fosnetupitant with a solution comprising cyclohexane to afford a mixture; (b) slurrying the mixture; (c) filtering the slurried mixture; and (d) isolating the crystalline solid.

Pharmaceutical Compositions and Methods of Making

The crystalline forms of the invention can be administered in the form of pharmaceutical compositions or dosage forms. These compositions can be prepared in a manner well known in the pharmaceutical art, and can be administered by a variety of routes depending upon whether local or systemic treatment is desired and upon the area to be treated. Administration can be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the crystalline form of the invention in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active crystalline form, soft and hard gelatin capsules, suppositories, sterile injectable solutions, and sterile packaged powders.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In a particularly preferred embodiment the crystalline forms of the present invention are used to manufacture an injectable dosage form as a liquid solution or a lyophilized powder produced from a liquid solution. The crystal forms of the present invention can be completely dissolved in the liquid solution, or they can continue to exist in crystalline form, or a combination of both. The liquid solution will typically comprise water and one or more pharmaceutically acceptable excipients. Examples of such excipients include tonicifying agents, preservatives, buffers, antioxidants, and pH adjusting agents. Thus, in one embodiment, the invention provides a method of making a pharmaceutical dosage form comprising mixing a crystalline form of the present invention with water and one or more pharmaceutically acceptable excipients to form a liquid solution, and optionally lyophilizing the liquid solution.

Methods of Treatment

The crystalline forms of Formula I are particularly useful for the treatment of diseases associated with substance-P activity. The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187-214), anxiety (Can. J. Phys., 1997, 75, 612-621) and depression (Science, 1998, 281, 1640-1645). Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases is well established ("Tachykinin Receptor and Tachykinin Receptor Antagonists", J. Auton. Pharmacol., 13, 23-93, 1993). NK-1 receptor antagonists, in particular, are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

NK-1 receptor antagonists are further useful for the treatment of motion sickness and for treatment induced vomiting. The New England Journal of Medicine, Vol. 340, No. 3 190-195, 1999 has been described the reduction of cisplatin-induced emesis by a selective neurokinin-1-receptor antagonist. U.S. Pat. No. 5,972,938 describes a method for treating a psychoimmunologic or a psychosomatic disorder by administration of a tachykinin receptor, such as NK-1 receptor antagonist. Furthermore, the crystalline forms of this invention are useful as agents against headache, anxiety, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases.

Some indications in accordance with the present invention are those which include disorders of the central nervous system, for example indications for the treatment or prevention of certain depressive disorders, anxiety or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

Further examples of NK-1-associated diseases include induced vomiting and nausea, including chemotherapy-induced nausea and vomiting (CINV) which is a common side effect of many cancer treatments. Further examples of NK-1-assocated diseases include overactive bladder disorder (OAB or urinary incontinence), which, in some cases, results from sudden, involuntary contraction of the muscle in the wall of the urinary bladder.

Combination Administration

The crystalline forms of the invention can also be formulated in combination with one or more additional active ingredients which can include any pharmaceutical agent such as antibodies, immune suppressants, anti-inflammatory agents, drugs used for the treatment of rheumatoid arthritis, disorders of the central nervous system and the like. In a particularly preferred embodiment, the crystalline forms of the present invention are formulated with a therapeutically effective amount of a 5-HT3 antagonist such as palonosetron hydrochloride.

EXAMPLES

In all the examples reported, unless otherwise reported, the starting compound was Form I of the chloride hydrochloride salt of 4-(5-(2-(3,5-bis(trifluoromethyl)phenyl)-N,2-dimethylpropanamido)-4-(o-tolyl)pyridin-2-yl)-1-methyl-1-((phosphonooxy)methyl)piperazin-1-ium, produced substantially according to the methods described in WO 2013/082102.

Example 1: Characterization of Fosnetupitant

1. Experimental Methods 1.1 Solubility

The solubility of the starting compound was determined in 25 pharmaceutically acceptable solvents (class II and III) of differing polarity. The procedure was as follows:

Approximately 20 mg of material was weighed out into each glass vial.

5 volume aliquots of each solvent were added separately with stirring (i.e. 1 volume=20 µl; hence, 5 volume=100 µl (5×20 µl)).

The mixture was stirred at RT for 5-10 minutes. Visual checks were then made for solubility.

If no solubility was achieved then steps (ii) and (iii) were repeated until either the solubility was achieved or the 50 volume aliquots of that solvent were added.

Solubility was then approximated.

Solubility was finally checked at the elevated temperature (40° C.).

1.2 Polymorph Screen (Including Slurry Studies)

Using the information from the solubility study, the compound was slurried in the solvents outlined in Table I and two more mixtures of water/MeOH (10:90) and water/Acetone (1:20) respectively with temperature cycling between 40° C. and RT (4 hour periods at each temperature) over 48 hours. After the slurries the resulting solids were isolated and analyzed by Raman and XRPD (where enough material was available) for any change in physical form.

The compound was also dissolved in the listed solvents and two more mixtures of water/organic solvent to yield saturated solutions, and crystallization was induced by: crash cooling (at ca. −18° C.); evaporation (at RT); and addition of an anti-solvent. Solid materials generated were then isolated and examined by Raman and XRPD (where enough material was available).

1.3 Scale-Up of any New Polymorphic Forms

Any new potential polymorphic forms of the Form I fosnetupitant were then scaled-up to ~500 mg level for further characterizations by PLM, SEM, DSC, TGA, GVS (XRPD post GVS) and NMR. Further studies of conversion between each polymorphic form were also performed. From this information, an understanding of the polymorphic space was achieved.

1.4 Stability Studies

The polymorphs identified were stored at 40° C./75% RH (open vial). Each sample was put in a glass vial un-capped. Analysis was carried out at 7 days by XRPD and Raman for any potential change in crystalline structure.

1.5 Competitive Slurries

The polymorphs identified were slurried in 4 solvents to determine which form is dominant at RT (c.a. 25° C.). Analysis was carried out after 2 days by Raman and confirmed by XRPD. Possible enantiotropic behavior was also examined by repeating the experiments at 50° C.

1.6 Aqueous Solubility of Polymorphic Forms of Form I Fosnetupitant

The aqueous solubility of the polymorphs of Form I fosnetupitant was determined in saturated solutions by HPLC.

1.7 Analytical Techniques 1.7.1 Polarized Light Microscope (PLM)

An Olympus BX50 microscope, equipped with an analyzer and polarizer, was used to observe each sample under polarized light. Micrographs of the sample were taken by using JVC-TKC1380 digital camera connected to a PC running Studio QuickStart version 9.3.2. A 20×/0.50 (magnifier/numerical aperture (NA) value) objective was used to view samples and capture images.

1.7.2 Raman

Samples were analyzed by a Nicolet Almega XR Dispersive Raman Microscope for its Raman spectrum using the following conditions:

Exposure Time: 1.0 s
Exposure Times: 10
Pinhole Size: 100 µm
Wavelength range: 4000~46 m$^{-1}$
Laser: 633 nm 100% power
Objective: 20×/0.40

Then the measured Raman spectra were corrected by baseline subtraction using the software OMNICTM v7.3.

1.7.3 X-Ray Powder Diffraction (XRPD)

Approximately 2 mg of sample was gently compressed on the XRPD zero back ground single obliquely cut silica sample holder. The sample was then loaded into a Philips X-Pert MPD diffractometer and analyzed using the following experimental conditions.

Tube anode: Cu
Generator tension: 40 kV
Tube current: 40 mA
Wavelength alpha1: 1.5406 Å
Wavelength alpha2: 1.5444 Å
Start angle (o): 5.000
End angle (o): 50.000
Step size (o): 0.0173
Time per step (sec): 31 seconds 1.7.4 Differential Scanning Calorimetry (DSC)

Approximately, 2 mg of each sample was weighed into an aluminum DSC pan and sealed non-hermetically with an aluminum lid. The sample was then loaded into a Perkin-Elmer Diamond DSC (equipped with a liquid-nitrogen cooling unit) cooled and held at 25° C. Once a stable heat-flow response was obtained, the sample was then heated to 300°

C. at a scan rate of 200° C./min and the resulting heat flow response monitored. A 20 cm³/min helium purge was used to prevent thermally induced oxidation of the sample during heating and also to reduce the thermal lag through the sample to increase the instrument sensitivity. Prior to analysis, the instrument was temperature and heat-flow calibrated using an indium reference standard.

1.7.5 Simultaneous Thermal Analysis (STA)

Approximately 2 mg of sample was put into a ceramic pan and loaded into a PerkinElmer STA 6000 held at room temperature. The sample was then heated at a rate of 10° C./min to 300° C. during which time the change in weight was monitored. In addition, DTA (Differential Thermal Analysis) (the same function as DSC) was monitored at the same time. The purge gas used was nitrogen at a flow rate of 20 cm³/min. Prior to analysis the instrument was weight calibrated using a 100 mg reference weight and temperature evaluated using an indium reference standard.

1.7.6 Gravimetric Vapor Sorption (GVS)

Approximately 20 mg of sample was placed into a wire-mesh vapor sorption balance pan and loaded into an 'IgaSorp' vapor sorption balance (Hiden Analytical Instruments). The sample was then dried by maintaining a 0% humidity environment until no further weight change was recorded. Subsequently, the sample was subjected to a ramping profile from 0-90% RH at 10% RH increments, maintaining the sample at each step until equilibration had been attained (99.5% step completion). Upon reaching equilibration, the % RH within the apparatus was ramped to the next step and the equilibration procedure repeated. After completion of the sorption cycle, the sample was dried using the profile from 85-5% RH at 10% RH increments same procedure. At last, the sample was dried by maintaining a 0% humidity environment until no further weight change was recorded. The weight change during the sorption/desorption cycles were then monitored, allowing the hygroscopic nature of the sample to be determined.

1.7.7 Nuclear Magnetic Resonance (NMR)

Solution (DMSO d6) 1H nuclear magnetic resonance (NMR) spectra were acquired with a Bruker Avance 400 spectrometer operating at 400.13 MHz, respectively. DMSO-d6 was used to dissolve the samples for NMR.

2 Results 2.1 Solubility Study

Using the method described in section 1.1, the solubility of the compound in the selected solvents was approximated and shown in Table 1.1.

TABLE 1.1

| solvent | Solubility (mg/ml) |
|---|---|
| EtOH | <21.9 |
| MeOH | >=119.5 |
| EtOAc | <14 |
| THF | <17.8 |
| Toluene | <18.2 |
| 1,4-Dioxane | <25.3 |
| Acetone | <22.7 |
| MeCN | <13 |
| iPA | <30.4 |
| DCM | <15 |
| MIBK | <15.9 |
| 2-BuOH | <24.4 |
| Diisopropyl ether | <20.9 |
| MeOAc | <12.3 |

TABLE 1.1-continued

| solvent | Solubility (mg/ml) |
|---|---|
| MTBE | <21.8 |
| Xylene | <16.7 |
| MEK | <24 |
| Dithyl Ether | <12.6 |
| 1-Pentanol | <14.3 |
| Chloroform | <28.4 |
| Cyclohexane | <11.3 |
| Pentane | <27.5 |
| Diisopropyl Acetate | <15.1 |
| Chlorobenzene | <28 |

The data in Table I showed that Form I of the compound has very poor solubility in most solvents except MeOH.

2.2 Primary Polymorphism Screen

After slurry using the procedure as described in section 1.2, the samples were initially checked by Raman and XRPD (where enough materials available) for any new crystalline forms. The solid materials isolated from crystallization screen, including crash cooling, anti-solvent addition (pentane was used as anti-solvent) and evaporation, were also checked by Raman and XRPD (where enough materials available) for new crystalline forms. The results are summarized in Table 1.2 as shown below:

TABLE 1.2

(Summary of Primary Polymorph Screen)

| | a) Slurry Slurry (40°/C./RT temperature Cycling) | | | |
|---|---|---|---|---|
| A | EtOH[1] | iPA[1] | MEK[2] | MeOH/H$_2$O (90/10) |
| B | MeOH | DCM[1] | Diethyl Ether[1] | Acetone/H$_2$O (20/1)[2] |
| C | EtOAc[1] | MIBK[2] | 1-Pentanol[1] | |
| D | THF[1] | 2-BuOH[1] | Chloroform[1] | |
| E | Toluene[1] | Diisopropyl ether[1] | Cyclohexane[3] | |
| F | 1,4-Dioxane[1] | MeOAc[1] | Pentane[1] | |
| G | Acetone[1] | MTBE[1] | Diisopropyl Acetate[1] | |
| H | MeCN[1] | Xylene[1] | Chlorobenzene[1] | |
| | b) Evaporation Evaporation (Evap) (at RT over N2) | | | |
| A | EtOH[1] | iPA | MEK | MeOH/H$_2$O (90/10)[1] |
| B | MeOH[1] | DCM | Diethyl Ether | Acetone/H$_2$O (20/1) |
| C | EtOAc | MIBK | 1-Pentanol | |
| D | THF | 2-BuOH | Chloroform | |
| E | Toluene | Diisopropyl ether | Cyclohexane | |
| F | 1,4-Dioxane | MeOAc | Pentane | |
| G | Acetone | MTBE | Diisopropyl Acetate | |
| H | MeCN | Xylene | chlorobenzene | |
| | c) Crash cooling Crash cooling (−18° C.)(CC) | | | |
| A | EtOH | iPA | MEK | MeOH/H$_2$O (90/10)[1] |
| B | MeOH[1] | DCM | Diethyl Ether | Acetone/H$_2$O (20/1) |
| C | EtOAc | MIBK | 1-Pentanol | |
| D | THF | 2-BuOH | Chloroform | |
| E | Toluene | Diisopropyl ether | Cyclohexane | |
| F | 1,4-Dioxane | MeOAc | Pentane | |
| G | Acetone | MTBE | Diisopropyl Acetate | |
| H | MeCN | Xylene | chlorobenzene | |

TABLE 1.2-continued (Summary of Primary Polymorph Screen)

d) Anti-solvent addition
Anti-solvent addition (AA)

| A | EtOH | iPA | MEK | MeOH/H$_2$O (90/10)[1] |
|---|---|---|---|---|
| B | MeOH[1] | DCM | DiEthyl Ether | Acetone/H$_2$O (20/1) |
| C | EtOAc | MIBK | 1-Pentanol | |
| D | THF | 2-BuOH | Chloroform | |
| E | Toluene | Diisopropyl ether | Cyclohexane | |
| F | 1,4-Dioxane | MeOAc | Pentane | |
| G | Acetone | MTBE | Diisopropyl Acetate | |
| H | MeCN | Xylene | chlorobenzene | |

[1]Form I obtained
[2]Form II obtained
[3]Form III obtained

The results in Table 1.2 indicated that from the solvents selected, Forms I, II and III of fosnetupitant are produced in primary polymorph screening experiments.

2.3 Secondary Polymorphism Screen and Physical Characterizations

A secondary polymorph screen was performed on scale-up to produce enough of the potential new forms identified in the primary screen for further characterization, i.e. the 'as prepared' Form I fosnetupitant was slurried in Acetone/H$_2$O (20/1) (producing Form II) and cyclohexane (producing Form III). The original Form I, Form II and III as prepared by slurry were then dried under vacuum at 40° C. for ~72 hours. For comparison, the samples were characterized by a number of techniques. A hydrated version of Form II was generated by various routes from Form I or III.

Form I Observations

The following observations can be drawn about Form I from the work performed:

Form I is a white solid powder material.

XRPD indicates that the material is crystalline, but with some amorphous content indicated by its 'hallo' type baseline. (FIG. 1)

Figure 2:
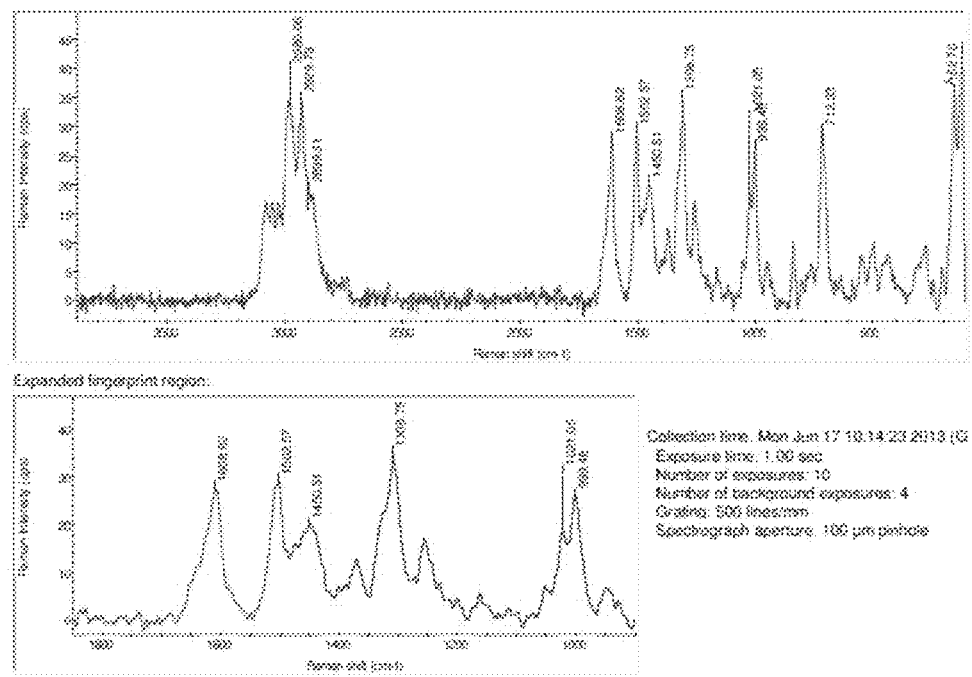
FIG. 2 is a Raman spectrum of Form I generated according to the procedures described in Example 1.

Raman shows that the material has a finger print (FP) of Raman below circa 1800. The material showed weak Raman signals and strong fluorescence. (FIG. 2)

PLM shows small irregular crystalline particles with some lumps of relatively larger particles, suggesting the sample being wet.

Figure 3:
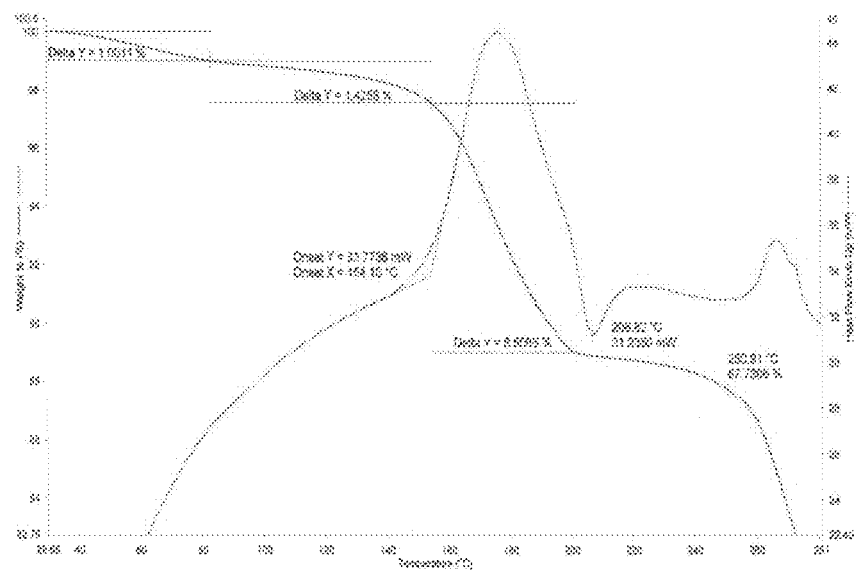
FIG. 3 is a Thermogravimetric Analysis (TGA) of Form I generated according to the procedures described in Example 1.

TGA on the as received and dried samples showed three (or two) steps of weight (Wt) loss on initial heating. Then the material changed to the parent drug followed by degradation upon further heating. Specifically, the Wt loss in each step changed from ca. 2.43 (=1.00+1.43) and 8.56% of three steps for the as received sample to ca. 3.55 and 8.71% of two steps for the dried sample respectively. The conversion of prodrug to parent drug started from ca. 152-154° C. followed by degradation at ca. 242-251° C. The simultaneous DTA data showed two endothermic (peak ca. 67° C. and ca. 152-154° C.) and one exothermic event (peak ca. 204-207° C.). (FIG. 3)

Figure 4:
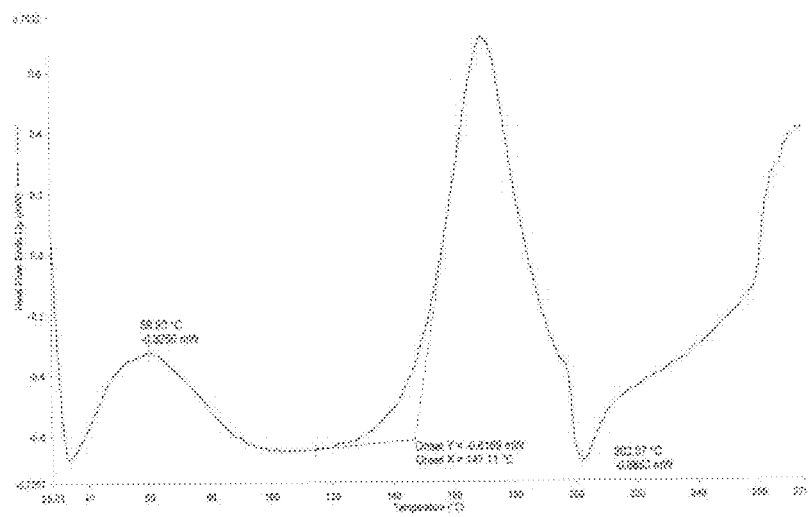
FIG. 4 is a Differential Scanning calorimetry (DSC) analysis of Form I generated according to the procedures described in Example 1.

DSC on original Form I sample showed two endothermic (peak ca. 60° C. and onset ca. 147° C.) and one exothermic event (peak ca. 202° C.) before degradation. (FIG. 4)

Figure 5:
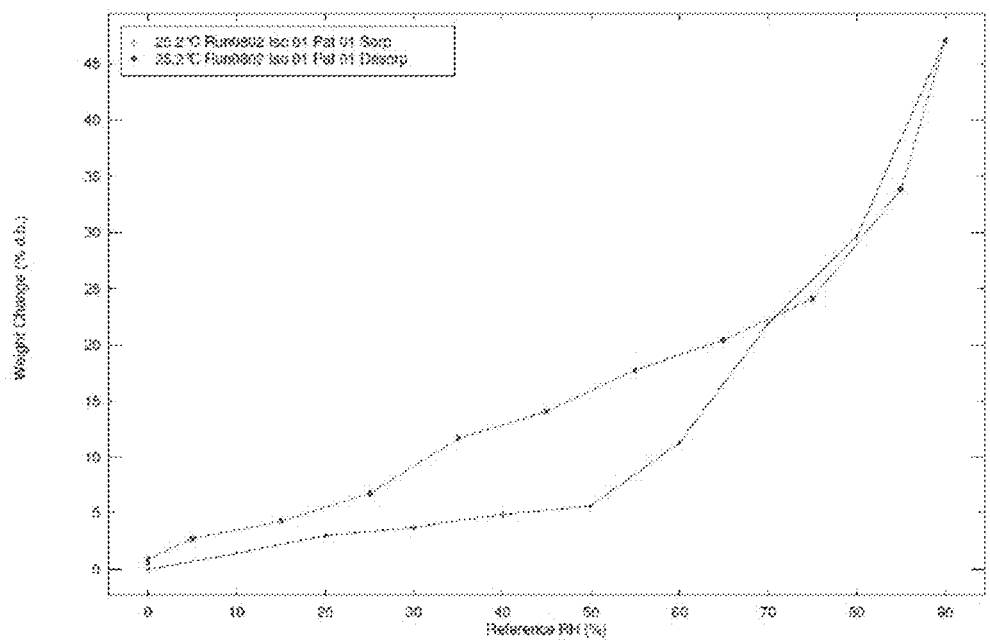
FIG. 5 is a Gravimetric Vapor Sorption (GVS) analysis of Form I generated according to the procedures described in Example 1.

GVS suggests a very hygroscopic (>15%@80% RH) material with an overall moisture uptake of about 45% w/w in the whole studied RH range up to 90% RH and about 5% from 0% to 50% RH (relative humidity). No form changes were detected by GVS. (FIG. 5)

Form II Observations

Form II is off-white solid powder material.

XRPD indicates that the material is crystalline, but with some amorphous content indicated by its 'hallo' type baseline. No significant change was found by XRPD between the as received and dried sample. (FIG. 6)

Figure 7:
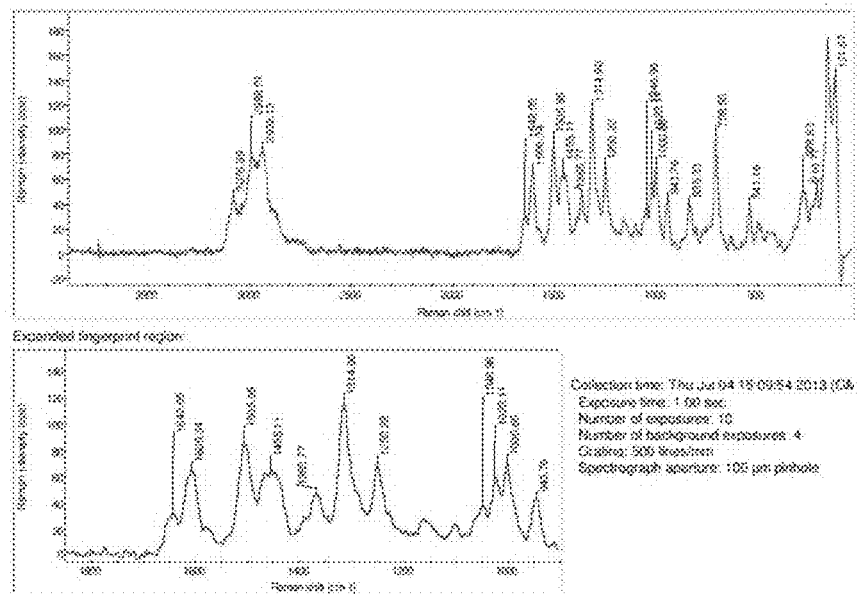
FIG. 7 is a Raman spectrum of Form II generated according to the procedures described in Example 1.

Raman shows that the material has a finger print (FP) of Raman below circa 1800 as well as the O—H (C—H) bond at the range of ca. 3000 m$^{-1}$. The material showed weak Raman signals and strong fluorescence. (FIG. 7)

PLM showed long rod crystalline particles, which also agrees with the result from primary screening.

Figure 8:
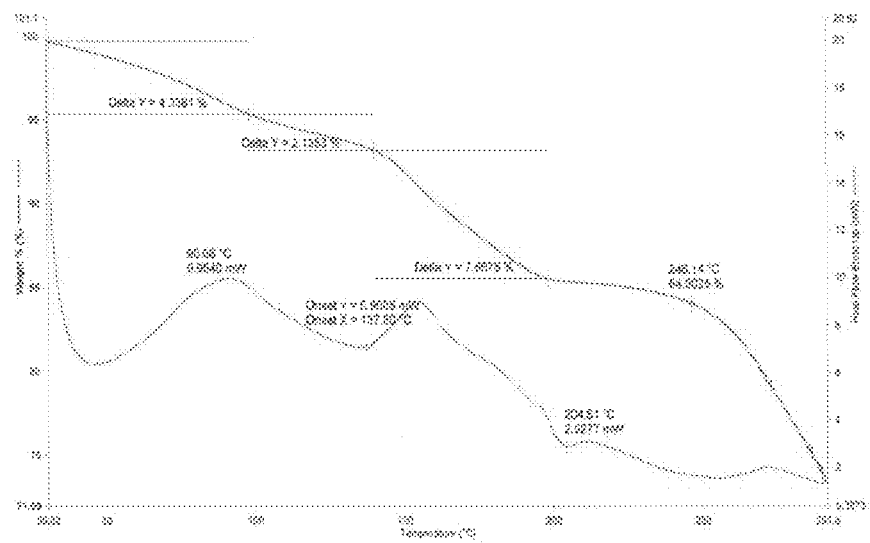
FIG. 8 is a Thermogravimetric Analysis (TGA) of Form II generated according to the procedures described in Example 1.

TGA on the as received and dried samples showed three (or two) steps of weight (Wt) loss on initial heating. Then the material changed to the parent drug followed by degradation upon further heating. Specifically, the Wt loss in each step changed from ca. 6.48 (=4.34+2.14) and 7.67% of three steps for the as prepared sample to ca. 4.22 and 7.54% of two steps for the dried sample respectively. The decrease in the initial Wt loss for the dried sample (from 6.48 to 4.22%) indicated some surface moisture was removed upon heating. The 2nd Wt loss could be assigned to the conversion of the prodrug to its parent drug. The conversion of prodrug to parent drug started from ca. 138-141° C. followed by degradation at ca. 240-246° C. The simultaneous DTA data showed two endothermic and one exothermic event before degradation (first peak ca. 91-101° C.; second onset ca. 138-141° C.). An exothermic event occurred at 203-205° C. (FIG. 8)

Figure 9:
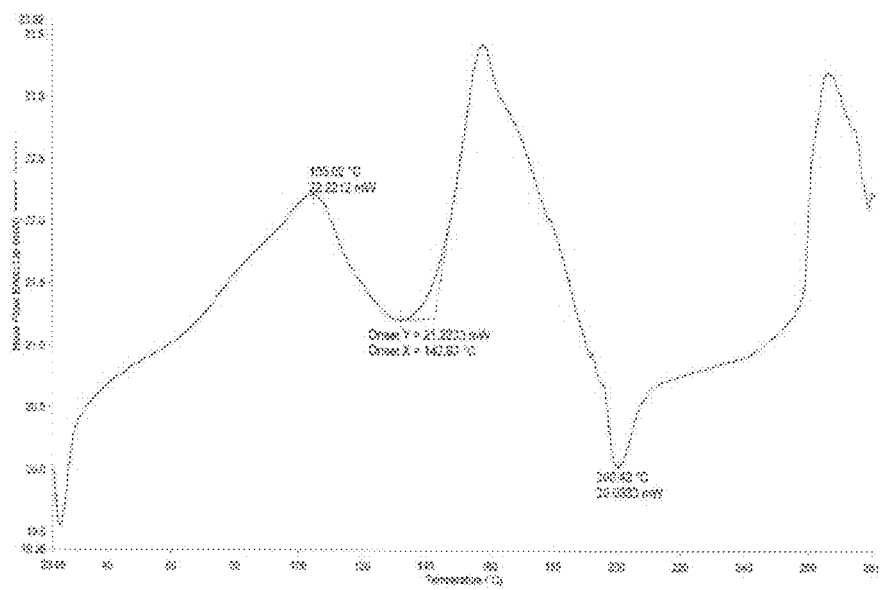
FIG. 9 is a Differential Scanning calorimetry (DSC) analysis of Form II generated according to the procedures described in Example 1.

DSC on the dried sample showed two endothermic and one exothermic events before degradation, an endothermic peak at ca. 105° C., an endothermic peak onset at ca. 143-147° C., and an exothermic peak at ca. 200° C. (FIG. 9)

Figure 10:
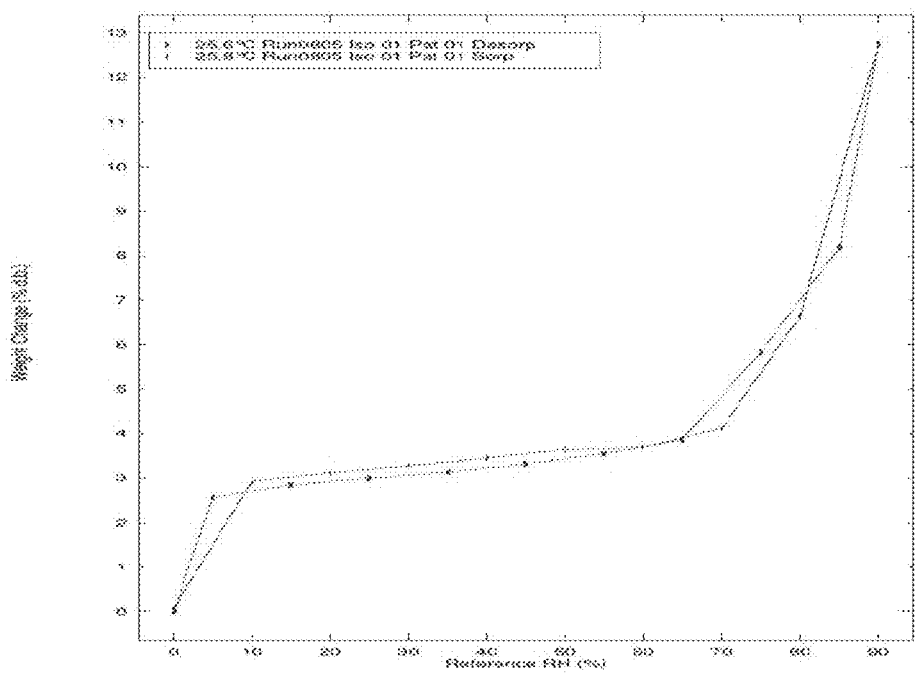
FIG. 10 is a Gravimetric Vapor Sorption (GVS) analysis of Form II generated according to the procedures described in Example 1.

GVS suggested a hygroscopic (15%>Wt increase>2%%@80% RH) material with an overall moisture uptake of circa 12.75% from 0% to 90% RH (relative humidity) and circa 4.12% from 0 to 70% RH. In absorption, the sharp Wt increase@10% RH was circa 2.92% w/w, suggesting potential hydration formed or significant amount of 'bulk' water absorbed. The gradual Wt increases of total circa 1.2% w/w was observed from 20 to 70% RH, suggesting surface wetting. The largest Wt increase of circa 8.63% w/w was from 70 to 90% RH, suggesting more moisture was absorbed by the material. GVS data also indicated a small loss of weight (~0.2% w/w) at 60% RH in the absorption process. (FIG. 10)

Form III Observations

Form III is a white solid powder material.

XRPD indicates that the material is crystalline, but with some amorphous content indicated by its 'hallo' type baseline. No significant change was found by XRPD between the as received and dried sample. XRPD data also showed the similarity between the crystalline structure of Forms I and III. (FIG. 11)

Figure 12:
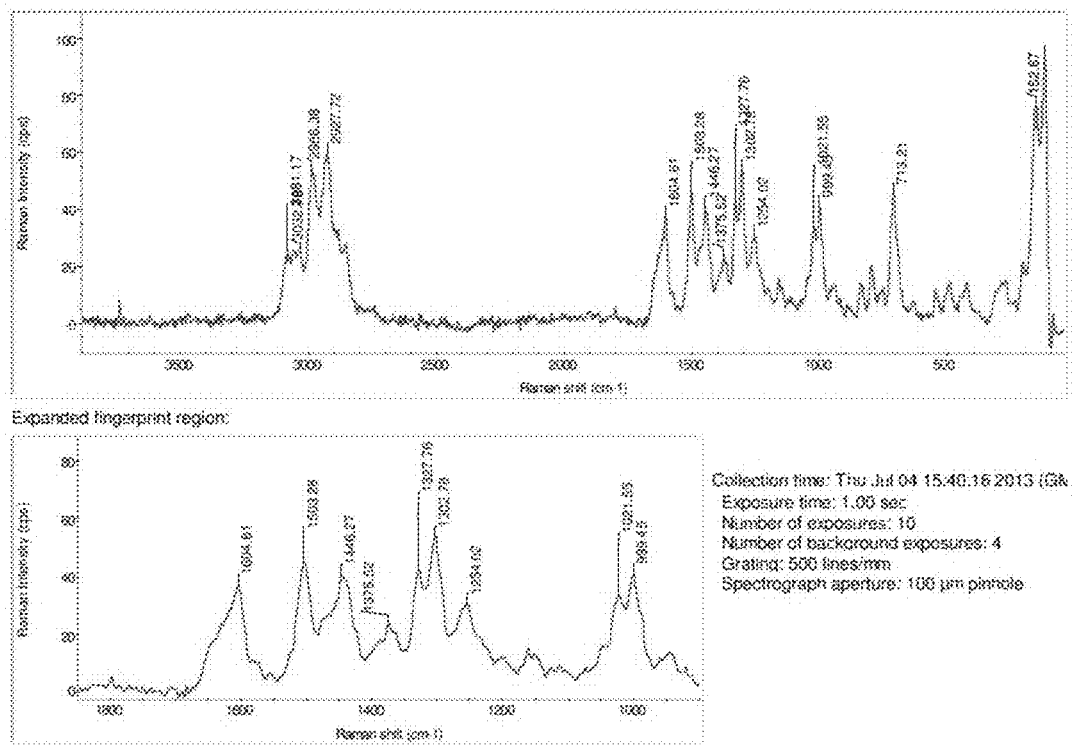
FIG. 12 is a Raman spectrum of Form III generated according to the procedures described in Example 1.

Raman shows that the material has a finger print (FP) of Raman below circa 1800. The material showed weak Raman signals and strong fluorescence. Raman data also showed the similarity between the crystalline structure of Forms I and III. (FIG. 12)

PLM showed small irregular crystalline particles, which also agrees with the result from primary screening.

Figure 13:
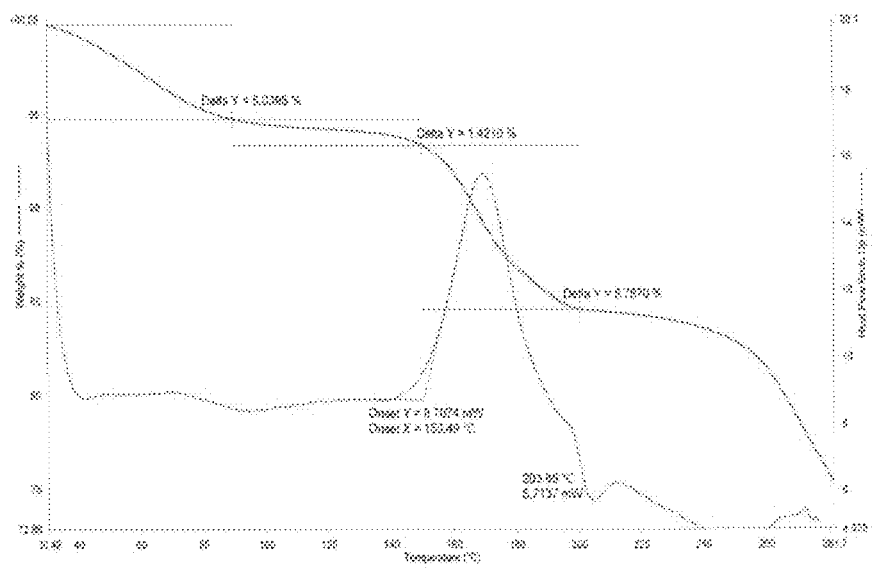
FIG. 13 is a Thermogravimetric Analysis (TGA) of Form III generated according to the procedures described in Example 1.

TGA on the as received and dried samples showed three (or two) steps of weight (Wt) loss on initial heating. Specifically, the Wt loss in each step changed from ca. 6.46 (=5.04+1.42) and 8.79% of three steps for the as prepared sample to ca. 2.76 and 8.82% of two steps for the dried sample respectively. The conversion of prodrug to parent drug started from ca. 146-150° C. followed by degradation at ca. 247-250° C. The simultaneous DTA data showed one or two endothermic and one exothermic event before degradation, an endothermic peak ca. 91-75° C., a second endothermic peak (onset ca. 146-150° C.), and an exothermic event (peak ca. 203-204° C.). (FIG. 13)

DSC on the dried sample showed two endothermic events and one exothermic event before degradation, at 65° C., at onset ca. 153° C., and at ca. 200° C., respectively.

GVS suggested a very hygroscopic (>15%@80% RH) material with an overall moisture uptake of circa 25% from 0% to 90% RH (relative humidity). The gradual Wt increases of total circa 5.19% w/w was observed from 0 to 50% RH, suggesting surface wetness. The largest Wt increase of circa 8.63% w/w was from 70 to 90% RH, suggesting more moisture was absorbed by the material. GVS data also indicated a large loss of weight (~5.82% w/w) at 80% RH in absorption process.

2.4 Stability Studies

Analysis at 7 days of the samples of each form stored at 40° C./75% RH open-vial by XRPD and Raman showed changes in crystalline structures of Form I and III but not Form II (stability studies as described in section 1.4).

The results are summarized in Table 2.4.

TABLE 2.4

(Stability Studies)
Stability Studies

| Sample ID | Materials | Condition | Time (h) | Generated form | Form checked by |
|---|---|---|---|---|---|
| 13PM712/19/1 | Form I | 40° C./75% RH | 1 week | changed (potentially to Form II) | XRPD, Raman |
| 13PM712/19/2 | Form II | | | No change | XRPD, Raman |
| 13PM712/19/3 | Form III | | | changed (potentially to Form II) | Raman |

2.5 Competitive Slurries

The mixtures of Forms I, II and III were respectively slurried in EtOH, EtOAc, iPA and 1,4-Dioxane at RT and 50° C. Analysis was performed after 2 days by Raman and XRPD (if necessary once the changes identified in Raman). The results are summarized in Table 2.5.

TABLE 2.5

(Results of Competitive Slurries)

| Sample ID | Materials | Solvent | Temperature | Time (h) | Generated Form | Form Checked by |
|---|---|---|---|---|---|---|
| a) Form I + II | | | | | | |
| Competative Slurry Studies (Form I + II) | | | | | | |
| 13PM712/20/1 | Form I + II | EtOH | 50° C. | 48 | Form III | Raman |
| 13PM712/20/2 | Form I + II | | RT | | Form III | |
| 13PM712/20/3 | Form I + II | EtOAc | 50° C. | | Form I + III | |
| 13PM712/20/4 | Form I + II | | RT | | Form I + III | |
| 13PM712/20/5 | Form I + II | iPA | 50° C. | | Form III | |
| 13PM712/20/6 | Form I + II | | RT | | Form I + III | |
| 13PM712/20/7 | Form I + II | 1,4 dioxane | 50° C. | | Form I + III | |
| 13PM712/20/8 | Form I + II | | RT | | Form I + III | |
| b) Form I + III | | | | | | |
| Competative Slurry Studies (Form I + III) | | | | | | |
| 13PM712/21/1 | Form I + III | EtOH | 50° C. | 48 | Form III | Raman |
| 13PM712/21/2 | | | RT | | | |
| 13PM712/21/3 | | EtOAc | 50° C. | | | |
| 13PM712/21/4 | | | RT | | | |
| 13PM712/21/5 | | iPA | 50° C. | | | |
| 13PM712/21/6 | | | RT | | | |
| 13PM712/21/7 | | 1,4 dioxane | 50° C. | | | |
| 13PM712/21/8 | | | RT | | | |
| c) Form II + II | | | | | | |
| Competative Slurry Studies (Form II + III) | | | | | | |
| 13PM712/22/1 | Form II + III | EtOH | 50° C. | 48 | Form III | Raman |
| 13PM712/22/2 | | | RT | | Form III | |
| 13PM712/22/3 | | EtOAc | 50° C. | | Form II + III | |
| 13PM712/22/4 | | | RT | | Form II | |
| 13PM712/22/5 | | iPA | 50° C. | | Form III | |
| 13PM712/22/6 | | | RT | | Form III | |
| 13PM712/22/7 | | 1,4 dioxane | 50° C. | | Form II + III | |
| 13PM712/22/8 | | | RT | | Form II + III | |

2.6 Aqueous Solubility of Two Polymorphic Forms of Form I Fosnetupitant

The aqueous solubility of Forms I and II is summarized in Table 2.6

TABLE 2.6.b

| (Solubility of Forms I and II at pH 12) | | | | | |
|---|---|---|---|---|---|
| Form I | | | Form II | | |
| immediately taken after all solid added | taken when no large particles seen (NTL 1 h) | Slurry NTL 24 h | immediately taken after all solid added | taken when no large particles seen (NTL 1 h) | Slurry NTL 24 h |
| 10.17 | 38.43 | 42.63 | 26.19 | 34.97 | 38.97 |

Example 2. Further Characterization of Forms I and II

Further XRPD characterization of Forms I and II was undertaken according to the following experimental details. FIGS. 14 and 15 depict the X-ray diffraction patterns taken from Form I; FIG. 16 depicts the X-ray diffraction pattern taken from Form II. Tables 2.A and 2.B list representative XRPD peaks obtained from Form I; Table 2.0 lists representative XRPD peaks obtained from Form II.

TABLE 2.A

| Pos. [°2Th.] | Height [cts] | FWHM [°2Th.] | d-spacing [A] | Rel. Int. [%] |
|---|---|---|---|---|
| 4.5369 | 3345.73 | 0.1171 | 19.47705 | 100.00 |
| 8.9896 | 2118.47 | 0.1171 | 9.83727 | 63.32 |
| 10.1782 | 170.71 | 0.1004 | 8.69104 | 5.10 |
| 12.6787 | 582.12 | 0.1673 | 6.98207 | 17.40 |
| 12.9151 | 391.93 | 0.1338 | 6.85974 | 11.71 |
| 13.4847 | 1023.91 | 0.1506 | 6.56647 | 30.60 |
| 14.2243 | 193.41 | 0.2007 | 6.22668 | 5.78 |
| 16.4418 | 419.53 | 0.2676 | 5.39153 | 12.54 |
| 17.1112 | 64.69 | 0.2007 | 5.18211 | 1.93 |
| 17.9834 | 1748.60 | 0.1338 | 4.93268 | 52.26 |
| 18.7020 | 143.04 | 0.1673 | 4.74475 | 4.28 |
| 20.1849 | 224.37 | 0.5353 | 4.39939 | 6.71 |
| 22.4862 | 270.76 | 0.1004 | 3.95409 | 8.09 |
| 23.4477 | 84.46 | 0.2342 | 3.79408 | 2.52 |
| 24.0106 | 121.78 | 0.2676 | 3.70638 | 3.64 |
| 25.5829 | 52.45 | 0.4015 | 3.48205 | 1.57 |
| 27.1709 | 161.30 | 0.2342 | 3.28205 | 4.82 |
| 28.6046 | 224.73 | 0.1673 | 3.12072 | 6.72 |
| 32.6707 | 118.31 | 0.5353 | 2.74102 | 3.54 |
| 36.3930 | 39.36 | 0.2007 | 2.46876 | 1.18 |

TABLE 2.B

| Pos. [°2Th.] | Height [cts] | FWHM [°2Th.] | d-spacing [A] | Rel. Int. [%] |
|---|---|---|---|---|
| 4.4924 | 2879.78 | 0.1004 | 19.67022 | 100.00 |
| 8.9576 | 1628.49 | 0.1171 | 9.87241 | 56.55 |
| 10.0851 | 150.79 | 0.2342 | 8.77108 | 5.24 |
| 12.6985 | 417.76 | 0.1338 | 6.97123 | 14.51 |
| 13.4695 | 603.40 | 0.1338 | 6.57384 | 20.95 |
| 14.1892 | 218.36 | 0.2007 | 6.24199 | 7.58 |
| 14.8619 | 64.56 | 0.2676 | 5.96093 | 2.24 |
| 16.3235 | 248.83 | 0.4684 | 5.43035 | 8.64 |
| 17.1318 | 74.59 | 0.2007 | 5.17591 | 2.59 |
| 17.9344 | 1230.04 | 0.1673 | 4.94606 | 42.71 |
| 18.6393 | 150.56 | 0.2007 | 4.76056 | 5.23 |
| 20.1276 | 110.84 | 0.2007 | 4.41179 | 3.85 |
| 22.4907 | 130.37 | 0.2676 | 3.95330 | 4.53 |
| 23.4186 | 162.98 | 0.1004 | 3.79872 | 5.66 |
| 25.5651 | 70.26 | 0.4684 | 3.48444 | 2.44 |
| 27.1138 | 221.65 | 0.1004 | 3.28883 | 7.70 |

TABLE 2.B-continued

| Pos. [°2Th.] | Height [cts] | FWHM [°2Th.] | d-spacing [A] | Rel. Int. [%] |
|---|---|---|---|---|
| 28.3574 | 146.19 | 0.1004 | 3.14736 | 5.08 |
| 32.8604 | 77.87 | 0.4015 | 2.72563 | 2.70 |

TABLE 2.C

| Pos. [°2Th.] | Height [cts] | FWHM [°2Th.] | d-spacing [A] | Rel. Int. [%] |
|---|---|---|---|---|
| 4.5773 | 63.74 | 0.2676 | 19.30518 | 3.53 |
| 6.0039 | 1710.37 | 0.0836 | 14.72097 | 94.60 |
| 6.3134 | 146.97 | 0.0836 | 13.99991 | 8.13 |
| 6.7452 | 225.77 | 0.0669 | 13.10465 | 12.49 |
| 7.0104 | 168.90 | 0.1004 | 12.60951 | 9.34 |
| 7.6447 | 1105.11 | 0.1004 | 11.56472 | 61.12 |
| 8.6336 | 92.70 | 0.0502 | 10.24217 | 5.13 |
| 8.9976 | 49.58 | 0.1338 | 9.82859 | 2.74 |
| 9.6576 | 218.02 | 0.0836 | 9.15832 | 12.06 |
| 11.3392 | 281.98 | 0.0836 | 7.80365 | 15.60 |
| 11.7554 | 83.74 | 0.0836 | 7.52828 | 4.63 |
| 11.9613 | 138.90 | 0.1004 | 7.39913 | 7.68 |
| 12.5126 | 144.85 | 0.1004 | 7.07436 | 8.01 |
| 12.8919 | 138.46 | 0.1004 | 6.86708 | 7.66 |
| 13.1654 | 183.48 | 0.1004 | 6.72504 | 10.15 |
| 13.8803 | 1201.54 | 0.1171 | 6.38023 | 66.45 |
| 14.0819 | 1137.50 | 0.1171 | 6.28931 | 62.91 |
| 14.5353 | 206.09 | 0.1171 | 6.09413 | 11.40 |
| 15.0909 | 199.71 | 0.0669 | 5.87101 | 11.05 |
| 15.3417 | 239.82 | 0.1171 | 5.77558 | 13.26 |
| 16.0183 | 136.29 | 0.1338 | 5.53312 | 7.54 |
| 16.5491 | 314.82 | 0.1004 | 5.35684 | 17.41 |
| 17.8733 | 1002.30 | 0.1171 | 4.96282 | 55.43 |
| 18.3749 | 851.10 | 0.1338 | 4.82846 | 47.07 |
| 18.8640 | 158.18 | 0.1004 | 4.70436 | 8.75 |
| 19.3688 | 1808.09 | 0.1004 | 4.58289 | 100.00 |
| 19.7884 | 182.64 | 0.1004 | 4.48665 | 10.10 |
| 19.9963 | 259.64 | 0.0669 | 4.44046 | 14.36 |
| 20.4247 | 512.70 | 0.1004 | 4.34829 | 28.36 |
| 20.6171 | 933.80 | 0.0836 | 4.30814 | 51.65 |
| 21.0330 | 186.17 | 0.1171 | 4.22388 | 10.30 |
| 21.3823 | 953.87 | 0.1338 | 4.15566 | 52.76 |
| 21.7228 | 132.28 | 0.1338 | 4.09129 | 7.32 |
| 22.0077 | 80.01 | 0.1004 | 4.03897 | 4.43 |
| 22.5119 | 95.48 | 0.1004 | 3.94963 | 5.28 |
| 22.7475 | 219.98 | 0.1338 | 3.90926 | 12.17 |
| 23.1827 | 526.35 | 0.1004 | 3.83684 | 29.11 |
| 23.8368 | 152.11 | 0.1004 | 3.73301 | 8.41 |
| 24.1140 | 444.01 | 0.1171 | 3.69073 | 24.56 |
| 24.3776 | 269.39 | 0.1004 | 3.65142 | 14.90 |
| 25.1404 | 360.55 | 0.0836 | 3.54232 | 19.94 |
| 26.0168 | 302.28 | 0.0836 | 3.42495 | 16.72 |
| 26.4005 | 261.27 | 0.1171 | 3.37605 | 14.45 |
| 26.8237 | 50.53 | 0.2676 | 3.32373 | 2.79 |
| 27.4323 | 172.66 | 0.0669 | 3.25136 | 9.55 |
| 28.3088 | 348.36 | 0.1338 | 3.15265 | 19.27 |
| 29.2231 | 203.80 | 0.0669 | 3.05607 | 11.27 |
| 29.9834 | 69.96 | 0.3011 | 2.98028 | 3.87 |

TABLE 2.C-continued

| Pos. [°2Th.] | Height [cts] | FWHM [°2Th.] | d-spacing [Å] | Rel. Int. [%] |
|---|---|---|---|---|
| 30.6197 | 166.54 | 0.1338 | 2.91978 | 9.21 |
| 31.1433 | 66.02 | 0.1004 | 2.87188 | 3.65 |
| 31.3739 | 71.39 | 0.1004 | 2.85130 | 3.95 |
| 31.8131 | 123.80 | 0.1004 | 2.81293 | 6.85 |
| 32.2024 | 71.51 | 0.2007 | 2.77980 | 3.96 |
| 32.088 | 52.00 | 0.2007 | 2.72173 | 2.88 |
| 33.3913 | 217.65 | 0.0669 | 2.68350 | 12.04 |
| 34.2500 | 17.63 | 0.2007 | 2.61816 | 0.98 |
| 35.1286 | 62.43 | 0.1338 | 2.55467 | 3.45 |
| 36.2625 | 73.68 | 0.1338 | 2.47735 | 4.07 |
| 36.5044 | 142.60 | 0.0836 | 2.46148 | 7.89 |
| 37.2105 | 80.38 | 0.1338 | 2.41638 | 4.45 |
| 37.8729 | 47.05 | 0.1338 | 2.37563 | 2.60 |
| 38.3456 | 150.63 | 0.0836 | 2.34742 | 8.33 |

2 Instrument Details 2.1 X-Ray Powder Diffraction (XRPD)
Instrument type: X'Pert PRO PANalytical
The X'Pert PRO X-ray diffraction system includes the following items:
  A console which provides the working environment for the X'Pert PRO system; it includes measuring and control electronics using a microprocessor system, and high tension generator.
  A ceramic diffraction X-ray tube, mounted onto the goniometer in a tube shield; the goniometer is described in section 4.1.1.
  A goniometer, the central part of the diffractometer; the goniometer is described in section 4.1.2.
  Optical modules for the incident and the diffracted X-ray beam. These modules can be mounted on PreFIX positions on the goniometer's arms.
  A sample stage on which to mount a sample so that its characteristics can be measured. Sample stage is the generic name given to any device onto which a sample is mounted so that it can be measured or analyzed. The sample stage used on X'Pert PRO system is the sample spinner. The purpose of spinning is to bring more crystallites into the diffraction position in order to reduce the influence of particle statistics on the measurements. The spinning rotation speed can be set at 2, 1, ½, ¼, ⅛, and ¹⁄₁₆ revolutions per second.
  A detector to measure the intensity of the diffracted X-ray beam; the goniometer is described in section 4.1.3.
2.1.1 Ceramic Diffraction X-Ray Tubes
General Tube Specifications
Focus type: LFF (Long Fine Focus)
Focus dimensions: 12 mm×0.4 mm
Focus quality: To COCIR specifications
Take-off angle (with no intensity loss over range)
line focus: 0°-12° (also dependent on shutter opening)
point focus 0°-20° (also dependent on shutter opening)
Be window diameter: 14 mm
Be window thickness: 300 μm
Power Characteristics
High power ceramic diffraction X-ray tube with copper anode
Maximum power: 2.2 kW
Maximum high tension: 60 kV
Maximum anode current 55 mA
Advised power settings: 80%-85% of maximum power
Advised standby ratings: 30-40 kV, 10-20 mA
Spectral Purity
Foreign lines measured with a β-filter
at 40 kV relative to the Kα line: On delivery<1%
Increase per 1000 hours of tube life: <1% for tubes with Cu anode
Environmental Conditions
Operating temperature: +5° C. to +40° C.
Storage temperature: −40° C. to +70° C.
Electrical safety: IEC1010-1
Cooling Water Conditions
Quality: Drinking water
Flow: 3.5-51/minute
Maximum pressure: 0.8 MPa
Pressure drop at 3.5 l/minute: 0.2+/−0.04 MPa
Max. Temperature: 35° C.
Min. Temperature: Depends on dew point of air
2.1.2 Goniometers X'Pert PRO
X'Pert PRO X-ray diffraction systems are based on the PW3065/6× Goniometer. The goniometer contains the basic axes in X-ray diffractometry: the θ and 2θ axes. PW3050/60 X'Pert PRO Standard Resolution Goniometer:
Operation mode Horizontal or vertical, θ-θ or θ-2θ mode
Reproducibility 0.0001°
0.001° (with attachments)
Scan speed: 0.000001-1.27°/s
Slew speed: 12°/s (with attachments)
Minimum step size: 0.001°
2θ range: −40°-+220°
θ range: −15°-+181°
2θ measurement range: Dependent on optics, geometry and sample stage
Diffractometer radius: 130-240 mm (X'Pert PRO MPD systems); 240 mm is standard setting
Distance goniometer
face-diffraction plane: 150 mm
X'Celerator
Used with: Line focus and point focus
Used in: All systems
Radiation type: Optimized for Cu radiation
99% linearity range: 0-900 kcps overall
0-7000 cps local
Maximum count rate: 5000 kcps overall
250 kcps local
Maximum background noise<0.1 cps
Typical energy resolution
for Cu Kα radiation 25%
Efficiency for Cu Kα 93%
Detector window size 15 mm parallel to the line focus
9 mm perpendicular to the line focus
Active length: 9 mm
(2.2° at 240 mm goniometer radius; 1.6° at 320 mm goniometer radius)
Smallest step size: 0.0021° at 240 mm goniometer radius
0.0016° at 320 mm goniometer radius
Operating modes: Scanning mode
  Receiving slit mode Other Embodiments From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All references cited herein, including patents, patent applications, and published patent applications, are hereby incorporated by reference in their entireties, whether or not each is further individually incorporated by reference.

The invention claimed is:

1. A method of making a crystalline form of the chloride hydrochloride salt of (4-(5-(2-(3,5-bis(trifluoromethyl)phenyl)-N,2-dimethylpropanamido)-4-(o-tolyl)pyridin-2-yl)-1-methylpiperazin-1-ium-1-yl)methyl hydrogen phosphate (fosnetupitant) which is Form I ("Form I fosnetupitant"), comprising less than 0.5 wt. % of impurities other than water and organic volatile impurities, comprising:
   a. contacting the chloride hydrochloride salt of fosnetupitant with methylacetate and methanol to form a first liquid;
   b. separating the methylacetate and methanol from the chloride hydrochloride salt of fosnetupitant of step (a);
   c. contacting the chloride hydrochloride salt of fosnetupitant from step (b) with heptane to form a second liquid; and
   d. separating the heptane from the chloride hydrochloride salt of fosnetupitant of step (c).

2. The method of claim 1 wherein:
   a. step (a) further comprises contacting said chloride hydrochloride salt of fosnetupitant with hydrochloric acid;
   b. step (b) comprises evaporating said methanol from said first liquid product of step (a);
   c. step (d) comprises evaporating said heptane from said second liquid at a pressure less than atmospheric and a temperature of from 20 to 50° C.

3. The method of claim 1 wherein, prior to step (a), said chloride hydrochloride salt of fosnetupitant is dissolved in methanol to form a solution, methanol is partially distilled from said solution, and methylacetate is added to said solution to form said first liquid.

4. A crystalline form of the chloride hydrochloride salt of (4-(5-(2-(3,5-bis(trifluoromethyl)phenyl)-N,2-dimethylpropanamido)-4-(o-tolyl)pyridin-2-yl)-1-methylpiperazin-1-ium-1-yl)methyl hydrogen phosphate which is Form II ("Form II fosnetupitant").

5. The crystalline form of claim 4 having an X-ray powder diffraction pattern comprising at least three peaks, in terms of 2θ, selected from the group consisting of 6.0, 6.7, 7.0, 7.6, 8.6, 9.7, 11.3, 11.8, 12.0, 12.5, 12.9, 13.2, 14.1, 15.3, 16.0, 16.5, 17.9, 18.4, 18.9, 19.4, 20.0, 20.6, 21.4, 21.7, 22.7, 23.2, 23.8, 24.4, 25.1, 26.0, 27.4, 28.3, 29.2, 30.6, 31.8, 33.4, 36.3, 37.2, 38.3°±0.2°.

6. The crystalline form of claim 4 having an X-ray powder diffraction pattern comprising at least three peaks, in terms of 2θ, selected from the group consisting of 6.0, 6.7, 7.6, 9.7, 11.3, 14.1, 15.3, 17.9, 18.4, 19.4, 20.0, 20.6, 21.4, 22.7, 23.2, 25.1, 26.0, 28.3, 29.2, 33.4°±0.2°.

7. The crystalline form of claim 4 having an X-ray powder diffraction pattern comprising at least three peaks, in terms of 2θ, selected from the group consisting of 6.0, 7.6, 14.1, 17.9, 19.4, 20.6, and 21.4°±0.2°.

8. The crystalline form of claim 4 characterized by the X-ray powder diffraction patterns shown in FIGS. 6 and 16.

9. The Form II fosnetupitant of claim 4 having a differential scanning calorimetry (DSC) thermogram characterized by an endotherm at 142.9±4° C.

10. The Form II fosnetupitant of claim 4 having a differential scanning calorimetry thermogram (DSC) substantially as shown in FIG. 9.

11. The crystalline form of claim 4, having a thermogravimetric analysis (TGA) substantially as shown in FIG. 8.

12. A composition comprising the Form II fosnetupitant of claim 4 and amorphous fosnetupitant.

13. A pharmaceutical composition comprising the Form II fosnetupitant of claim 5 and one or more pharmaceutically acceptable excipients.

14. A method of making a pharmaceutical composition comprising admixing the Form II fosnetupitant of claim 5 and one or more pharmaceutically acceptable excipients.

15. A process for preparing the Form II fosnetupitant of claim 5 comprising:
   a. combining the chloride hydrochloride salt of fosnetupitant with a solution comprising acetone and water to provide a mixture;
   b. slurrying the mixture;
   c. filtering the slurried mixture; and
   d. isolating a crystalline solid of Form II fosnetupitant.

16. A crystalline form of the chloride hydrochloride salt of (4-(5-2-3,5-bis(trifluoromethyl)phenyl)-N,2-dimethylpropanamido)-4-(o-tolyl)pyridin-2-yl)-1-methylpiperazin-1-ium-1-yl)methyl hydrogen phosphate which is Form III ("Form III fosnetupitant").

17. The Form III fosnetupitant of claim 16 characterized by the X-ray powder diffraction patterns shown in FIG. 11.

18. The Form III fosnetupitant of claim 16 having a differential scanning calorimetry (DSC) thermogram characterized by an endotherm at 153.0±4° C.

19. The Form III fosnetupitant of claim 16 having a thermogravimetric analysis (TGA) substantially as shown in FIG. 13.

20. A composition comprising the Form III fosnetupitant of claim 16 and amorphous fosnetupitant.

21. A pharmaceutical composition comprising the Form III fosnetupitant of claim 16 and one or more pharmaceutically acceptable excipients.

22. A method of making a pharmaceutical composition comprising admixing the Form III fosnetupitant of claim 16 and one or more pharmaceutically acceptable excipients.

23. A process for preparing the Form III fosnetupitant of claim 16 comprising combining the chloride hydrochloride salt of fosnetupitant with a solution comprising cyclohexane to afford a mixture;
   a. slurrying the mixture;
   b. filtering the slurried mixture; and
   c. isolating the crystalline solid.

* * * * *